United States Patent [19]

Ogawa et al.

[11] Patent Number: 5,372,851
[45] Date of Patent: Dec. 13, 1994

[54] METHOD OF MANUFACTURING A CHEMICALLY ADSORBED FILM

[75] Inventors: Kazufumi Ogawa, Hirakata; Norihisa Mino, Settu; Mamoru Soga, Osaka; Hidetaka Higashino, Soraku, all of Japan

[73] Assignee: Matsushita Electric Industrial Co., Ltd., Osaka, Japan

[21] Appl. No.: 984,478

[22] Filed: Dec. 2, 1992

[30] Foreign Application Priority Data

Dec. 16, 1991 [JP] Japan ................................. 3-332328
Dec. 19, 1991 [JP] Japan ................................. 3-337317

[51] Int. Cl.$^5$ .................................................. C23C 14/24
[52] U.S. Cl. ............................ 427/255.7; 427/333; 427/537
[58] Field of Search ............... 427/419.8, 419.7, 419.1, 427/412.1, 409, 408, 407.2, 533, 535, 537, 333, 255.7

[56] References Cited

U.S. PATENT DOCUMENTS

| | | | |
|---|---|---|---|
| 2,557,786 | 6/1951 | Johannson | 427/407.2 |
| 4,539,061 | 9/1985 | Sagiv | 427/407.1 |
| 4,810,564 | 3/1989 | Takahashi et al. | 428/213 |
| 4,961,996 | 10/1990 | Carre et al. | 428/421 |

FOREIGN PATENT DOCUMENTS

| | | |
|---|---|---|
| 0282188A1 | 9/1988 | European Pat. Off. . |
| 0484746A2 | 5/1992 | European Pat. Off. . |
| 0501298A2 | 9/1992 | European Pat. Off. . |

*Primary Examiner*—Shrive Beck
*Assistant Examiner*—Erma Cameron
*Attorney, Agent, or Firm*—Fish & Richardson

[57] ABSTRACT

This invention aims to form uniformly and effectively an ultra thin chemical adsorbing film having an excellent water repellent property, oil repellent property, and contamination-proof property on the surface of a substrate by chemically adsorbing in a gas phase atmosphere. A chemically adsorbed film can be formed on any type of substrate and in a short time by chemically adsorbing a chlorosilane based surface-active agent on the surface of a substrate having active hydrogen groups. Further, a chemically adsorbed monomolecular film, or a polymer film, can be formed on any type of substrate and in a short time by forming a siloxane based monomolecular film or a polysiloxane adsorbed film in a gas atmosphere having a chlorosilane based surface-active agent having plurality of chlorosilyl groups.

19 Claims, 5 Drawing Sheets

METHOD OF MANUFACTURING A CHEMICALLY ADSORBED FILM

FIELD OF THE INVENTION

This invention relates to a method of forming a chemically adsorbed film on the surface of a substrate. More particularly, it relates to a method of forming a chemically adsorbed monomolecular film or a chemically adsorbed polymer film in a gas phase atmosphere. The invention also relates to a method of laminating a chemically adsorbed monomolecular film or a polymer film via a siloxane based chemically adsorbed monomolecular film or via a siloxane based chemically adsorbed polymer film.

BACKGROUND OF THE INVENTION

Previously, the LB method (Langmuir Blodgett method) or a liquid phase adsorption method was used to form a monomolecular film. In the LB method, a straight chain molecule having a hydrophilic group and a water-repelling group are layered on a water surface, and the water is manipulated to deposit the layer on a substrate surface. In the LB method, which is essentially a wet process, a monomolecular film is fixed to the substrate by only Van der Waals' force, and the mechanical strength is weak. The chemical adsorption method using a liquid phase is a method of forming a monomolecular film via silicon bonding. The method includes dipping and holding a substrate in a non-aqueous solvent in which a molecule containing a carbon chain and an active silane group at one end is reacted with an active hydrogen of a hydroxyl group on the surface of the substrate. The principle of forming a chemically adsorbed monomolecular film in the above solution is to form a monomolecular film by initiating a dehydrochlorination reaction between a hydroxyl group on the surface of the substrate and a chlorosilyl group of the chlorosilane based adsorbent. In this manufacturing method, a monomolecular film can be obtained by dipping and holding a substrate such as a metal in an adsorptive liquid in a which chlorosilane based surface active material is dissolved in a non-aqueous solvent. (For reference, see the specification of U.S. Pat. No. 4,673,474, J. Am. Soc. 1983, 105, 674–676 (Sagiv), "Thin solid Films", 99 (1983) 235–241(Sagiv), "The American Physical Society" Vol.39, No.7 (1989)).

The chemically adsorbed monomolecular film, which can be obtained by the above method, bonds to the surface of the substrate via a strong chemical bond. The film does not separate from the substrate as long as the surface of the substrate is not scraped. However, this method is a wet process, utilizing a chemical reaction in a solvent in the liquid state. The chemical adsorption method using a liquid phase requires two to three hours to absorb at room temperature and to form a satisfactory adsorbing film since the adsorbing reagent is diluted with solvent. In addition, in the wet method, the types of solvent and substrates for adsorption are very severely limited since some of substrates can be damaged by the solvent or hydrochloric acid which is generated during the adsorption reaction.

Furthermore, the diluted solvent often contains minute particles of dust, and pinholes are easily generated in an ultra thin film. In addition, the substrate itself may swell or be dissolved by some types of diluted solvents.

Furthermore, in forming a monomolecular film by the wet process mentioned above, contamination of the liquid solution cannot be easily avoided. For example, in forming a monomolecular film for an electronic device, such as an insulated film for a condenser, electronic, optical or precision parts such as a protective film for a laser disk, contamination must be avoided as much as possible. In forming a thin film by deposition on a monomolecular film, the wet process requires washing and drying of the substrate. As a result, contamination and the number of days are increased.

On the other hand, there are dry processes for forming organic ultra thin films, such as plasma polymerization and vacuum deposition methods. In these methods, the types of molecules which can be obtained are limited very severely, and forming a monomolecular film can be very difficult.

This invention provides a method of forming a monomolecular film by a method using a gas phase to solve the above problems.

Furthermore, this invention aims to provide a method in which the type of substrate is not limited, an adsorbing solvent is not required, and an adsorbed film can be formed effectively in a short time. This invention prevents pinholes and forms a chemically adsorbed, uniformly thin film firmly on a substrate. This film formation is also more efficient.

SUMMARY OF THE INVENTION

An object of the invention is to provide a method of forming a chemically adsorbed film in a gas phase on a surface of a substrate containing active hydrogen groups comprising the steps of contacting a substrate surface with a silane based surface adsorbent having a reactive silyl group at one end and initiating a condensation reaction in a gas phase atmosphere.

It is preferable in this invention that the chlorosilane based adsorbent or an alkoxyl silane based adsorbent is used as the silane-based surface adsorbent and a dehydrochlorination reaction or a de-alcohol reaction is carried out as the condensation reaction.

It is preferable in this invention that after the dehydrochlorination reaction, the unreacted chlorosilane-based adsorbent on the surface of the substrate is washed, removed with a non-aqueous solution to form a monomolecular adsorbed film, and reacted with water.

It is preferable in this invention that after the dehydrochlorination reaction, a compound containing a straight chain molecule as the chlorosilane-based adsorbent is reacted with water to form a chemically adsorbed polymer film.

It is preferable in this invention that the chlorosilane-based surface adsorbent contains a straight fluorocarbon chain molecule or a portion of straight hydrocarbon chain molecule substituted by a $-CF_2$-group or a fluorocarbon based group.

It is preferable in this invention that the chlorosilane-based adsorbent is $CF_3-(CF_2)_n-(R)_m-SiX_pCl_{3-p}$ wherein n represents 0 or an integer; R represents an alkyl group, a vinyl group, an ethynyl group or a substituted group containing a silicon atom or an oxygen atom; m represents 0 or 1; X represents H, an alkyl group, an alkoxyl group, an alkyl substituted group containing fluorine or an alkoxyl substituted group containing fluorine; and p represents 0, 1, or 2.

It is preferable in this invention that the silane based adsorbent is $CF_3-(CF_2)_n-(R^1)_m-SiX_qOR^2_{3-q}$ wherein n represents 0 or an integer; $R^1$, and $R^2$ each represents an alkoxyl group an alkyl group, a vinyl group, an ethynyl group or a substituted group containing a silicon atom or an oxygen atom; m represents 0 or 1; X represents H, an alkyl group, an alkoxyl group, an alkyl substituted group containing fluorine or an alkoxyl substituted group containing fluorine; and q represents 0, 1, 2 or 3.

It is preferable in this invention that the substrate is selected from the group consisting of metal, ceramics, glass, plastic, a semiconductor, an inorganic shaped solid and an organic shaped solid.

It is preferable in this invention that a plastic substrate surface is hydrolized by treating with plasma containing oxygen or in a corona atmosphere.

It is preferable in this invention that the surface of the substrate is contacted with an alkoxyl silane based surface adsorbent and is heated to at least about 50° C. to initiate the condensation reaction.

Another object of the invention is to provide a method of forming a chemically adsorbed film in a gas phase comprising initiating a dehydrochlorination reaction between a substrate surface containing active hydrogen groups and an adsorbent gas of a material containing a plurality of chlorosilyl groups, washing and removing unreacted adsorbent with a non-aqueous solvent, forming a siloxane based monomolecular inner layer film containing a plurality of silanol groups on the surface of the substrate by reacting the inner layer with water, initiating a dehydrochlorination reaction between the inner layer film and an adsorbent gas of a material containing a straight chain group and a chlorosilane group at one end, washing and removing the unreacted adsorbent from the outer layer film with a non-aqueous organic solvent to form a laminated a monomolecular outer layer film, and stabilizing the outer layer with water.

A further object of the invention is to provide a method of forming a chemically adsorbed film in a gas phase comprising initiating a dehydrochlorination reaction between a surface of a substrate containing active hydrogen groups and an adsorbent gas to form an inner layer film by using an adsorbent gas of a material containing a plurality of chlorosilyl groups, forming a siloxane based polymer inner layer film containing a plurality of silanol groups on a surface of the substrate by reacting with water, initiating a dehydrochlorination reaction between an active hydrogen atom of the surface of the inner layer film and an adsorbent gas of a material containing a straight chain group and a chlorosilane group at one end, washing and removing unreacted adsorbent from the outer layer film with a non-aqueous organic solvent to form an outer layer film, stabilizing the outer layer with water.

A further object of the invention is to provide a method of forming a chemically adsorbed film in a gas phase comprising contacting an adsorbent gas of a material containing a plurality of chlorosilyl groups with a surface of a substrate containing active hydrogen groups to initiate a dehydrochlorination reaction between said active hydrogen groups and the adsorbent gas to form an inner monomolecular layer film, washing unadsorbed adsorbent with a non-aqueous organic solvent, reacting the inner layer with water to form a siloxane based monomolecular inner layer film containing a plurality of silanol groups on the surface of the substrate, contacting an adsorbent gas of a material containing a straight chain group and a chlorosilane group at one end with the surface of the inner layer film, and reacting the outer layer with water to form a laminated polymer outer layer film, and stabilizing the outer layer with water.

A further object of the invention is to provide a method of forming a chemically adsorbed film in a gas phase comprising contacting an adsorbent gas of a material containing a plurality of chlorosilyl groups with a surface of a substrate containing active hydrogen groups by bringing about a dehydrochlorination reaction between the active hydrogen groups and the adsorbent gas to form an inner layer film, reacting the inner layer with water to form a polysiloxane inner layer film containing a plurality of silanol groups, contacting an adsorbent gas of a material containing straight chain molecules having chlorosilane groups at one end with the inner layer film to form a laminated polymer outer layer film, and reacting to stabilize the outer layer with water.

It is preferable in this invention that the adsorbent comprising a plurality of chlorosilyl groups is at least one compound selected from the group consisting of $SiCl_4$, $SiHCl_3$, $SiH_2Cl_2$ or $Cl—(SiCl_2O)_n—SiCl_3$ wherein n represents an integer.

A still further object of the invention is to provide a method of forming a chemically adsorbed film in a gas phase wherein the chemically adsorbed film is formed on a surface of a substrate having active hydrogen groups comprising placing said substrate in a vacuum vessel at decreased pressure or in a vacuum vessel having a dry atmosphere and contacting a silane based surface adsorbent having a reactive silyl group at one end and in a gas phase with the surface of the substrate to bring about a dehydrochlorination reaction.

It is preferable in this invention that the silane based surface adsorbent have a plurality of chlorosilyl group.

It is preferable in this invention that the vessel is evacuated after contacting with the adsorbent.

It is preferable in this invention that the gas phase of the surface adsorbent is produced by heating the silane based surface adsorbent or bubbling the silane based surface adsorbent or the adsorbent solution containing a silane based adsorbent by using a dry inert gas as a carrier.

It is preferable in this invention that the vacuum vessel is at a decreased pressure lower than at least $10^{-5}$ Torr.

It is preferable in this invention that the active gas is contacted with the substrate after a step of exhaust.

It is preferable in this invention that the moisture in the air is used as a reactive gas.

It is preferable in this invention that the surface of substrate is irradiated by an ultraviolet rays at the same time when the reactive gas is introduced.

It is preferable in this invention that the silane based surface adsorbent is $CF_3—(CF_2)_p—(R)_m—SiCl_nX_{3-n}$, wherein p represents 0 or an integer, m represents 0 or 1, R represents a hydrocarbon group containing a methylene group, vinylene group (—CH=CH—), an ethynylene group (—C≡C—), a silicon group (—Si), or an oxygen atom (—O—), X represents a hydrogen atom, a lower alkyl group or a lower alkoxyl group, n represents an integer from 0 to 3.

It is preferable in this invention that the adsorbent having a plurality of chlorosilyl groups are selected from the group consisting of $SiCl_4$, $SiHCl_3$, $SiH_2Cl_2$, $Cl—(SiCl_2O)_n—SiCl_3$ wherein n represents an integer.

It is preferable in this invention that the substrate surface is reacted with moisture after dehydrochlorination to form an inner layer film, and the inner layer film is reacted with a silane based surface adsorbent containing fluorine in a gas phase to form an outer layer film, and the outer layer film is stabilized with moisture.

DETAILED DESCRIPTION OF THE INVENTION

Figure 1:
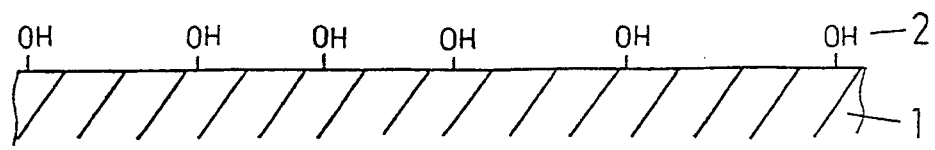
FIG. 1 is a sectional figure view showing the surface of a substrate which is enlarged to the molecular level.

According to one aspect of forming a chemically adsorbed film of the invention, an adsorbed film can be formed on the surface of a substrate by contacting a silane based surface adsorbent having an active silicon group at one end with the surface of a substrate in a gas phase atmosphere to cause a condensing reaction. According to the method mentioned above, an adsorbing solvent is not required and a pinhole-free adsorbing film can be formed having a uniformly thin thickness on the surface of substrate in a short time, effectively. A chemically adsorbed film can be formed more effectively and with a higher reaction by using a chlorosilane based adsorbent or an alkoxysilane based adsorbent as the silane based surface adsorbent and by using a dehydrochlorination reaction or a de-alcohol reaction as the condensing reaction. A monomolecular film can be formed effectively in the gas phase by washing with a non-aqueous organic solution to remove unreacted chlorosilane based adsorbent from the surface of the substrate after the dehydrochlorination reaction, and then reacting with water. An adsorbed polymer film can be formed in the gas phase by using a compound containing a straight chain molecule as the chlorosilane based adsorbent and by reacting with water after the dehydrochlorination reaction without washing with a non-aqueous organic solution to remove unreacted chlorsilane based adsorbent from the surface of the substrate.

In using an alkoxysilane based adsorbent, the alkoxysilane based adsorbent can be chemically bonded to the surface of substrate effectively by heating the substrate at least about 50° C., preferably 70° C. to 150° C. after deposition.

According to another aspect of the invention, a pinhole-free chemically adsorbed monomolecular laminated film having a uniformly ultra thin thickness, which is excellent in heat-resistance and durability as a monomolecular outer layer film, is formed by chemically bonding layers of a monomolecular layer film through a siloxane inner monomolecular layer film on a substitute surface.

According to another aspect of the invention, a pinhole-free chemically adsorbed film, which is excellent in heat-resistant and durability, can be formed as a monomolecular outer layer film by chemically bonding a monomolecular layer film through a siloxane polymer inner layer film on the surface of a substrate.

According to another aspect of the invention, a pinhole-free thin film, which is excellent in heat-resistance and durability and is uniformly ultra thin in thickness, can be formed as an outer polymer layer film which is bonded to a monomolecular inner siloxane based monomolecular layer film which is formed on the surface of substrate, and bonded to the substrate via siloxane bonds (covalent bonds).

Further, according to another aspect of the invention, a pinhole-free and chemically adsorbed polymer film having a uniformly ultra thin thickness, which is excellent in heat-resistance and durability, can be formed as an outer polymer layer film which is bonded through a polymer inner layer film by chemical bonds on the surface of a substrate.

Where, by adsorbing and layering the straight chain molecule as a silane based adsorbent containing a chlorosilane group, a dehydrochlorination reaction is brought about between —OH groups of an inner polysiloxane based monomolecular film, or polymer film, which has numerous —SiOH groups and which are formed on the surface of a substrate in the step above-mentioned, and an outer monomolecular layer film, or a polymer film, is chemically bonded to the substrate via —SiO bonds. As a result, a chemically bonded outer layer film is formed which is extremely excellent in close adherence.

According to another aspect of the invention, after removing atoms or molecules which cause contamination on the surface of a substrate by decreasing pressure such as by evacuation, a silane based surface adsorbent having an active silane group at one end and a material containing a straight carbon chain having a plurality of chemical bonds of chlorine and a silicon group (a chlorosilane group; —SiCl$_n$X$_{3-n}$, represents 1, 2, 3 and X represents a functional group: chemical adsorbent) are introduced to the surface of the substrate or to the surface of a chemically adsorbed film beforehand to chemically react with hydrophilic groups on the surface of the substrate or chemically adsorbed film to form siloxane bonds. Thus, a monomolecular layer film can be formed. As a result, contaminants that may be in the monomolecular film can be decreased. In previous methods, a chemical adsorbent was dissolved in a great amount of solvent. Thus, a chemically adsorbed film was easily effected by the purity of the solvent. On the other hand, according to the invention, the lower level of contamination depends only on the degree of purity of chemical adsorbent. Thus contamination can be decreased by increasing the degree of purity of the chemical adsorbent.

Further, water or hydrogen chloride molecules are not an obstacle to chemical adsorption, since the water or hydrogen chloride can be easily removed by diffusing. Chemical adsorption is completed when hydrophilic group reaction sites have run out. After forming a chemically adsorbed monomolecular film, a monomolecular film having a uniform thickness can be obtained by evacuation to remove unreacted chemically adsorbed molecules which is physically adsorbed on the surface of chemically adsorbing film. Then, a monomolecular film can be formed automatically.

By using a material containing a straight carbon chain having a plurality of chemical bonds of chlorine and silicon ($-SiCl_nX_{3-n}$ group, n represents 1, 2, 3 and X represents a functional group), a chemically adsorbed film can be laminated on a substrate surface within a vacuum vessel by introducing water vapor as the reactive gas or introducing hydrogen gas and oxygen gas and irradiating with ultraviolet rays to react with unreacted chemical bonds of chlorine and silicon to form a silanol group after evacuation to remove a material containing unreacted chemical bonds of chlorine and silicon. Then, contamination of the laminated chemically adsorbing film can be avoided.

A substrate having hydroxyl groups including: a metal, such as Al, Cu, stainless steel, ceramics; glass; plastic; a semiconductor; an inorganic shaped solid; an organic shaped solid; and other hydrophilic substrates on the surface can be used in this invention.

A substrate having no hydroxyl groups on the surface can be used in the invention by pre-treating the surface of the substrate at 100 W for twenty minutes in a plasma atmosphere including oxygen, or treating the surface of substrate with corona to hydrolyze, i.e., introduce hydroxyl groups to the surface of substrate. Polyamide resin and polyurethane resin do not need surface treatment since they have imino groups (>NH) on the surface. The hydrogen of the imino group (>NH) and chlorosilyl group of the chemical adsorbent are used to bring about dehydrochlorination to form a siloxane bond, $SiCl_4$, $SiHCl_3$, $SiH_2Cl_2$, and $Cl-(SiCl_2O)_n-SiCl_3$ (n represents an integer) can be used as a material containing chlorosilyl group to form an inner layer film in the invention.

It is preferable to use $SiCl_4$ since the molecule is small and reactive with hydroxyl groups. Thus a great effect of hydrolizing a surface of a substrate can be obtained. Non-aqueous gas such as dry nitrogen can be used as the gas atmosphere having a material containing a chlorosilyl group.

1 wt % to 100 wt % (adsorptive atmosphere) of material containing a chlorosilyl group can be used. However, the density of material containing a chlorosilyl group depends on the type of material. The substrate which is left in the adsorptive atmosphere for about thirty minutes and a dehydrochlorination reaction is brought about on the substrate surface to fix the material containing a chlorosilyl group by adsorption. A siloxane based monomolecular film (inner layer film) can be formed after washing well with a non-aqueous solvent, and by reacting with water to remove a material containing unreacted chlorosilyl groups. A polysiloxane film can be formed without washing with a with non-aqueous solvent after fixing a material containing chlorosilyl group by adsorption.

In forming a surface layer film, as numerous hydroxyl groups are formed on the surface of inner layer film, the hydroxyl groups can be reacted with a hydrocarbon based adsorbent having a chlorosilyl group or a fluorocarbon based adsorbent. When the surface of the substrate is highly hydrophilic, the surface layer film can be formed on the surface of the substrate directly, and forming an inner layer film is not necessary.

The substrate which is left in an atmosphere of a hydrocarbon based adsorbent having chlorosilyl groups or a fluorocarbon based adsorbent (1 wt% to 100 wt % of atmosphere of hydrocarbon based solvent containing chlorosilyl groups or fluorocarbon based adsorbent can be used. However, the density of the atmosphere depends on the material containing the chlorosilyl group or the type of solvent) for about thirty minutes to bring about a dehydrochlorination reaction with numerous hydrophilic —OH groups contained on the surface of the substrate to fix the hydrocarbon based adsorbent having chlorosilyl groups or a fluorocarbon based adsorbent by adsorption. A monomolecular film (outer layer film) can be formed by washing well with a non-aqueous solvent and then by reacting with water to remove hydrocarbon based adsorbent containing unreacted chlorosilyl groups or the fluorocarbon based adsorbent. A polymer film of a fluorocarbon based adsorbent having chlorosilyl groups can be formed by the step abovementioned without washing with a non-aqueous solvent after fixing the hydrocarbon based adsorbent or the fluorocarbon based adsorbent by adsorption. The reaction is also brought about by a dehydrochlorination reaction.

A compound containing a fluorocarbon group and a chlorosilane group can be used as adsorbent to form a surface layer film. $CF_3-(CF_2)_n-(R)_m-SiX_pCl_{3-p}$ (where n represents 0 or an integer, preferably 1 to 22, R represents an alkyl group, a vinyl group, an ethynyl group, a substituted group containing a silicon or oxygen atom, m represents 0 or 1, X represents H, an alkyl group, or an alkyl group containing fluorine, and p represents 0 or 1 or 2.) can be used. It is preferable to use a compound containing fluorine and a chlorosilyl group to obtain a water, and oil repellent property, a contamination-proof property and a lubricating property at the substrate surface.

A hydrocarbon based chemical adsorbent can be used as a chemical adsorbent to form a surface layer film. Examples of a chemical adsorbent are shown below.

$CH_3-(CH_2)_r SiX_pCl_{3-p}$, $CH_3-(CH_2)_s O(CH_2)_t SiX_pCl_{3-p}$, $CH_3-(CH_2)_u-Si(CH_3)_2(CH_2)_v-SiX_pCl_{3-p}$, $CH_3COO(CH_2)_w SiX_pCl_{3-p}$, $CF_3-(CF_2)_r SiX_pCl_{3-p}$, $CF_3-(CF_2)_s(CH_2)_t SiX_pCl_{3-p}$, $CF_313 (CF_2)_s O(CH_2)_t SiX_pCl_{3-p}$, $CF_3-(CF_2)_u-Si(CH_3)_2(CH_2)_v SiX_pCl_{3-p}$, $CF_3COO(CH_2)_w SiX_pCl_{3-p}$. (where r preferably represents 1 to 25, s preferably represents 0 to 12, t preferably represents 1 to 20, u preferably represents 0 to 12, v preferably represents 1 to 20, w preferably represents 1 to 25.)

Examples of another chemical adsorbent are shown below.

$CF_3-(CF_2)_n-(R^1)_m-SiX_qOR^2_{3-q}$ (wherein n represents 0 or an integer, $R^1$, $R^2$ represents an alkoxyl group, an alkyl group, a vinyl group, an ethynyl group or a substituted group containing a silicon atom or an oxygen atom, m represents 0 or 1, X represents H, an alkyl group, an alkoxyl group, an alkyl substituted group containing fluorine or an alkoxyl substituted group containing fluorine, and q represents 0, 1, 2 or 3.)

In addition to the adsorbents abovementioned, more examples of adsorbents will be shown concretely.

The invention can widely be applied to the following surfaces. Materials made of pottery, porcelain, ceramics, glass, plastic, wood, or stone etc. are applicable as the substrate. The surface of the substrate may be also coated with paint or the like in advance.

Examples of ceramics cutlery include: a kitchen knife, scissors, a knife, a cutter, a graver, a razor, hair clippers, a saw, a plane, a chisel, a gimlet, a badkin, a bit (cutting tools), a drill tip, an edge of a mixer, a juicer, a blade of a mill, a blade of a lawn mower, a punch, a straw cutter, a staple of a stapler, a can opener or a surgical knife and the like.

Examples of products in the pottery industry include: products made of pottery, glass, ceramics or enameled products. Specific example include, sanitary potteries (a chamber pot, a wash-bowl, a bathtub, etc.), tableware (a rice-bowl teacup, a dish (plate), a bowl, a teacup, a glass, a bottle, a coffee-pot (siphon), a pan, an earthenware mortar, (a cup and the like), vases (a flower bowl, a flowerpot, a bud vase and the like), water tanks (a breeding cistern, an aquarium water tank and the like). chemical experiment appliances (a beaker, a reactor vessel, a test tube, a flask, a laboratory dish, condenser, a mixing rod, a stirrer, a mortar, a bat, a syringe, etc.) a bath tile, a roof tile, enameled ware, an enameled washbowl, an enameled kettle, an enameled pan and the like.

Examples of ceramics molding parts: dies for press molding, dies for cast molding, dies for injection molding, dies for transfer molding, dies for compression molding, dies for transfer molding, dies for inflation molding, dies for vacuum molding, dies for blow forming, dies for extrusion molding, dies for fiber spinning, a calendar processing roll and the like.

Examples of plastics or ceramics forming molds for food include: cake pans, cookie trays, bread-baking pans, chocolate molds, jelly molds, ice cream molds, oven ware, ice trays and the like.

Examples of resin(s) include: a polyolefin such as a polypropylene and polyethylene, a polyvinylchloride plastic, a polyamide, a polyimide, polycarbonate, a polystyrene, a polysulfide, a polysulfone, a polyethersulfone, a polyphenylenesulfide, a phenolic resin, a furan resin, a urea resin, an epoxy resin, a polyurethane, a silicon resin, an ABS resin, a methacrylic resin, an acrylate resin, a polyacetal, a polyphenylene oxide, a polymethylpentene, a melamine resin, an alkyd resin, an unsaturated polyester cured resin and the like, Examples of rubber include: a styrene-butadiene rubber, a butyl rubber, a nitril rubber, a chloroprene rubber, a polyurethane rubber, a silicon rubber and the like.

Examples of ceramics, plastic or resin coating household electric appliances include: a refrigerator, a freezer, an air conditioner, a juicer, a mixer, a blade of an electric fan, a lighting apparatus, a dial plate, a dryer for a perm and the like.

Examples of plastic sporting goods include: skis, a fishing rod, a pole for the pole vault, a boat, a yacht, a surfboard, a fishing line, a float and the like.

Examples applying to vehicle parts:
(1) ABS resin: a lamp cover, an instrument panel, trimming parts, a protector for a motorcycle.
(2) Cellulose plastic: a car mark, a steering wheel
(3) FRP (fiber reinforced plastics): a bumper, an engine cover (jacket)
(4) Phenolic resin: a brake
(5) Polyacetal: wiper gear, a gas valve
(6) Polyamide: a radiator fan
(7) Polyarylate (polycondensation polymerization by bisphenol A and pseudo phthalic acid): a direction indicator lamp (or lens), a cowl board lens, a relay case
(8) Polybutylene terephthalate (PBT): a rear end, a front fender
(9) Poly amino-bismaleimide: engine parts, a gear box, a wheel, a suspension drive system
(10) Methacrylate resin: a lamp cover lens, a meter pannel and its cover, a center mark
(11) Polypropylene: a bumper
(12) Polyphenylene oxide: a radiator grill, a wheel cap
(13) polyurethane: a bumper, a fender, an installment pannel, a fan
(14) Unsaturated polyester resin: a body, a fuel tank, a heater housing, a meter pannel.

Examples of plastic or resin coating office supplies include: a desk, a chair, a bookshelf, a rack, a telephone stand table, a rule (measure), a drawing instrument and the like.

Examples of building materials include: materials for a roof, an outer wall and interiors. Roof materials include brick, slate and the like. Outer wall materials include wood (including processed manufactured wood), mortar, concrete, ceramic sizing, brick, stone, and plastic. Interior materials include such as wood (including processed wood), plastic, a paper and the like.

Examples of building stones include: granite, marble and others for use as a building, a building material, an architectural fixture, an ornament, a bath, a grave stone, a monument, a gatepost, a stone wall, a paving stone and the like.

A chemically adsorbed film can be formed on the surface of a substrate by forming a siloxane bond by chemically reacting hydrophilic groups on the surface of the substrate with the silane based surface adsorbent. The substrate is placed in a vacuum vessel and exposed to a silane based adsorbent having a reactive silane group at one end, which is in a gas phase. The gas phase silane based surface adsorbent is produced by heating the adsorbent or by bubbling using a dehydrated and inert gas such as argon or nitrogen as carrier. Then a monomolecular film having a uniform thickness can be formed by evacuating the vessel to remove unreacted silane based surface adsorbent.

Other embodiments of forming a monomolecular film in a gas phase according to the invention will be described as follows.

In one embodiment, the step of forming a monomolecular film includes an adsorbing step, a removing step and a step of forming a monomolecular film. In the adsorbing step, after placing a substrate having a hydrophilic group at the surface in a vacuum vessel, a material containing a straight chain carbon chain having a plurality of chemical bonds of chlorine and silicon ($-SiCl_nX_{3-n}$ group, n represents 1, 2, 3 and X represents a functional group) is introduced to the surface of substrate in a gas phase and is adsorbed on the substrate.

In the removing step, after the adsorbing step, a material containing a unadsorbed chemical bond of chlorine and silicon on the surface of substrate is removed by evacuating the vessel.

In the step of forming a monomolecular film, a monomolecular film containing a silanol group can be formed by reacting an unreacted chemical bond of chlorine and silicon which is contained in the material having the chemically adsorbed bond of chlorine and silicon abovementioned.

Another embodiment includes a step of forming a chemically adsorbed film in which a chemically adsorbed film can be laminated by repeating the step of forming the monomolecular adsorbing film abovementioned several times.

Another embodiment includes a step of laminating a chemically adsorbed monomolecular film in which after the step of forming an inner chemically adsorbed film, an outer monomolecular film can be formed by heating a silane based surface adsorbent having a reactive silane group at one end or by bubbling a silane based surface adsorbent having a reactive silane group at one end by using a dehydrated and inert gas such as argon or nitrogen as a carrier gas, which is to be exposed to the surface of the chemically adsorbed film to chemically react with the silanol groups to form siloxane bonds.

It is effective to use water vapor or hydrogen gas and oxygen gas with irradiating ultraviolet rays as active gas abovementioned.

Examples and FIGS. 1 to 7 are used to describe the invention. In the examples, % represents wt % except where specifically noted.

EXAMPLE 1

Figure 2:
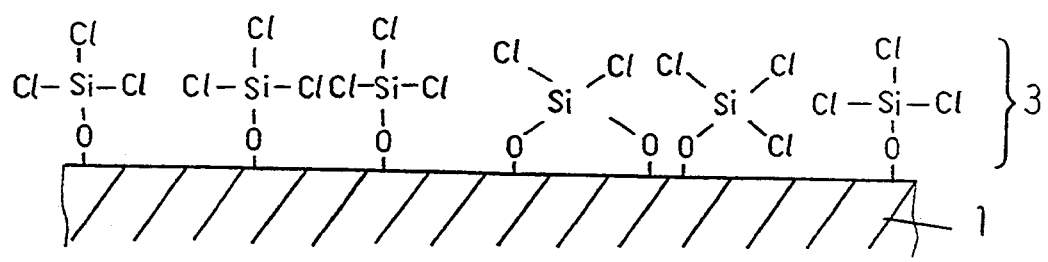
FIG. 2 is a sectional view showing the forming of a chlorosilane based monomolecular film on the surface of a substrate, which is enlarged to a molecular level.

An aluminum substrate 1 was used (FIG. 1). The adsorbing atmosphere (a chlorosilane adsorbing atmosphere) was made by vaporizing tetrachlorosilane (SiCl$_4$) as an adsorbent to form an inner siloxane layer film at room temperature in an adsorbing vessel which was purged by using dry nitrogen. In the chlorosilane adsorbing atmosphere abovementioned, an aluminum substrate 1, on which surface a few hydrophilic —OH groups were exposed, was left for about thirty minutes to bring about a dehydrochlorination reaction on the surface as shown in FIG. 2. The molecules were fixed on the surface of the substrate via —SiO— bonds as shown in formula 1 and/or formula 2.

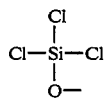

[Formula 1]

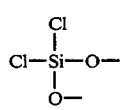

[Formula 2]

Figure 3:
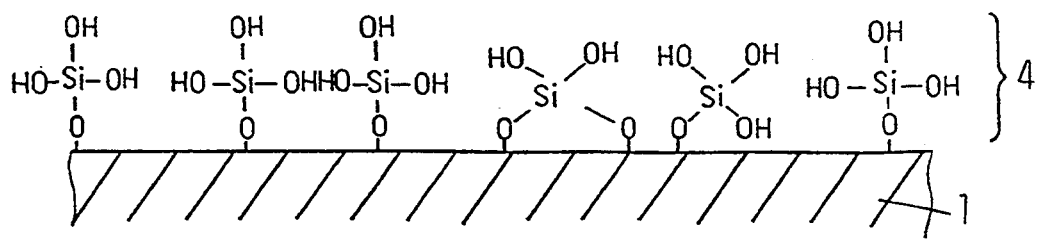
FIG. 3 is a sectional view showing an intermediate step of forming an inner film of siloxane based monomolecular film on the surface of a substrate, which is enlarged to a molecular level.

The siloxane monomolecular film 4 containing numerous silanol groups on the surface of substrate as shown in FIG. 3 was obtained by washing with a non-aqueous solvent such as chloroform, and then with water to remove unreacted SiCl$_4$ molecules, and by reacting the adsorbent with water. The siloxane monomolecular film 4 containing numerous silanol groups is shown in formula 3 and/or formula 4. A polysiloxane film containing numerous silanol groups was also obtained by the step abovementioned without washing with a non-aqueous solvent.

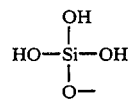

[Formula 3]

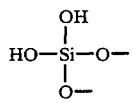

[Formula 4]

The obtained siloxane monomolecular film 4, or polysiloxane film, was perfectly bonded to the substrate via covalent bonds and did not separate at all.

The obtained monomolecular film 4, or polysiloxane film, had numerous —SiOH bonds on the surface. About three times as many hydroxyl groups on the substrate surface were generated compared to the initial number of —OH groups. Then a surface layer film was formed in the vessel which was purged using a non-aqueous gas. For example, straight carbon chain chemical adsorbents containing a fluorocarbon group and a chlorosilane group such as CF$_3$(CF$_2$)$_7$(CH$_2$)$_2$SiCl$_3$ were vaporized in a nitrogen gas atmosphere (a fluorocarbon adsorbing atmosphere).

The bonds as shown in formula 5 were formed on the surface of the substrate on which surface a siloxane inner monomolecular film or a polysiloxne inner polymer film was formed as shown in formula 4 by depositing the fluorocarbon adsorbent for about thirty minutes, and by washing the substrate with a non-aqueous solvent to remove unreacted molecules of CF$_3$(CF$_2$)$_7$(CH$_2$)$_2$SiCl$_3$, and by reacting the adsorbent with water.

[Formula 5]

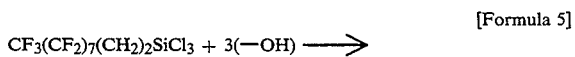

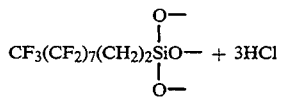

Figure 4:
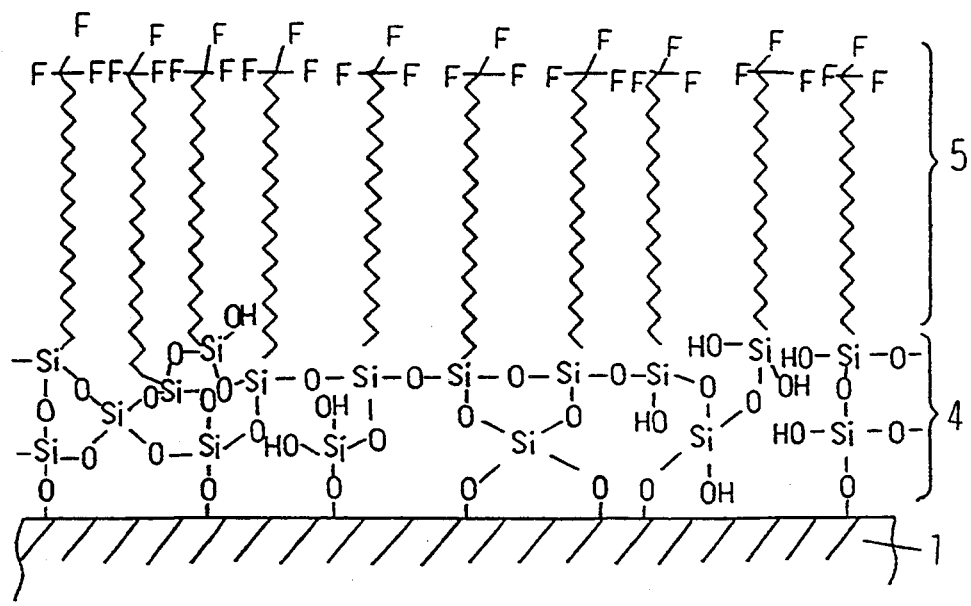
FIG. 4 is a sectional view showing a laminated layer film of a fluorocarbon based monomolecular film on an inner layer film of the surface of a substrate, which is enlarged to the molecular level.

FIG. 4 shows the bonding condition of molecules which were generated on the surface of the siloxane monomolecular film 4. As shown in FIG. 4, the outer monomolecular layer film 5 was formed by chemical bonds (covalent bonds) with an inner layer of the siloxane monomolecular film 4.

A fluorocarbon based outer polymer film was also formed on the surface of the siloxane inner monomolecular layer film or of the inner polysiloxane film by the abovementioned process without washing with a non-aqueous solvent. Further, the obtained monomolecular film was not separated at all by cross cut test.

In the abovementioned example, CF$_3$(CF$_2$)$_7$(CH$_2$)$_2$SiCl$_3$ fluorocarbon based adsorbent was used as the straight carbon chain molecule adsorbent to form an outer layer film. The hardness of the surface layer film can be improved by adding and by incorporating vinyl groups or ethynyl groups to the alkyl chain portion of CF$_3$(CF$_2$)$_7$(CH$_2$)$_2$SiCl$_3$, and the obtained monomolecular chemical adsorption film can be cross linked by irradiating with an electron beam of 5 Mega rads (Mrads).

Further, in this invention, although an adsorbent which is used to form a surface layer film is not limited to an adsorbent containing fluorine, a fluorocarbon based ultra thin film having a high mechanical strength is effective.

EXAMPLE 2

Figure 5:
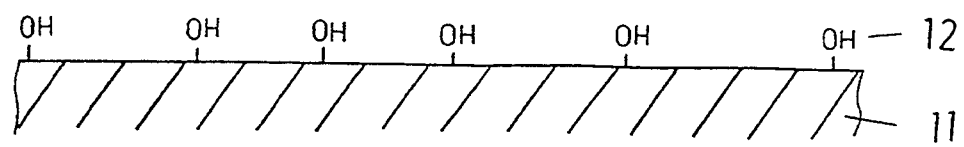
FIG. 5 is a sectional view showing the surface of a substrate, which is enlarged to the molecular level.

A back mirror 11, as shown in FIG. 5, using an acrylic resin for a transparent portion was used in example 2. As the surface of the acrylic resin had a water repellent property, the surface of acrylic resin was treated to be hydrophilic by applying 100 w of electric power in plasma containing oxygen for about thirty minutes. The surface of the acrylic resin abovementioned became hydrophilic but the ratio of hydroxyl groups was very low. Thus, octachlorosiloxane (shown in formula 6), a material containing a plurality of chlorosilyl group, was used as an adsorbent for forming an inner siloxane layer film.

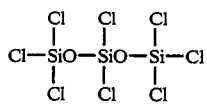  [Formula 6]

Figure 6:
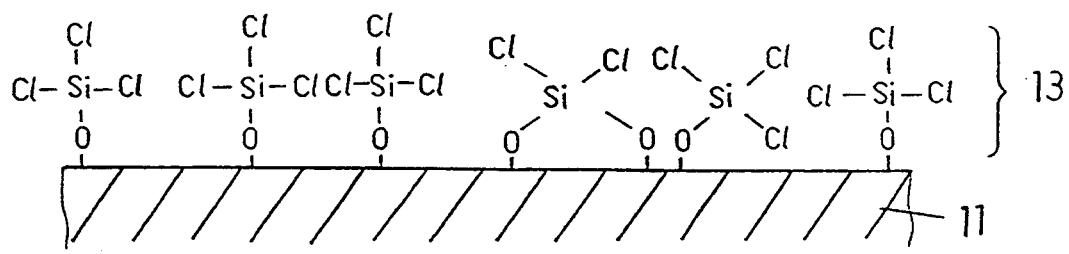
FIG. 6 is a sectional view showing the forming a chlorosilane based monomolecular film on the surface of a substrate, which is enlarged to the molecular level.

The adsorbent for forming the inner layer film (shown in formula 6) was dissolved in a non-aqueous solvent, Freon 113 solvent with a ratio of 30%, and was vaporized in the adsorbing vessel (Chlorosilane adsorbing atmosphere). The substrate was left in the chlorosilane adsorbing atmosphere for about thirty minutes to react with hydrophilic —OH groups 12 on the surface of the back mirror 11 (i.e., dehydrochlorination reaction). The unreacted adsorbent were washed with Freon 113 and removed to form a chlorosilane monomolecular film as shown in FIG. 6. Even if the surface of the back mirror 11 contained a little hydrophilic —OH groups, a dehydrochlorination reaction was brought about by using the adsorbent as the material containing plurality of chlorosilyl groups (shown in FIG. 6) to fix molecules on the surface of the back mirror via —SiO— bonds as shown in formula 7 and/or formula 8.

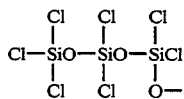  [Formula 7]

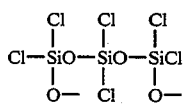  [Formula 8]

Figure 7:
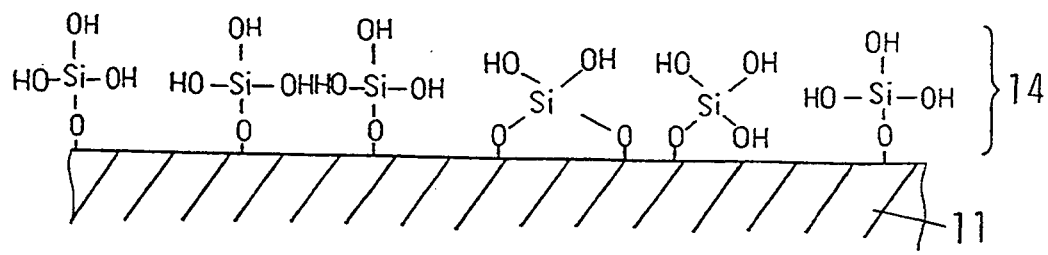
FIG. 7 is a sectional view showing an intermediate step of forming an inner layer film of a siloxane based monomolecular film on the surface of a substrate, which is enlarged from the molecular level.

Then, in general, unreacted adsorbent remained on chlorosilane monomolecular film 13. The surface of the back mirror 11 was washed with a non-aqueous solvent, such as Freon 113 to remove unreacted molecules, and then with water to form a siloxane monomolecular film 14 as shown in formula 9 and/or formula 10 on the surface of the back mirror 11 as shown in FIG. 7.

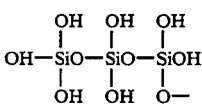  [Formula 9]

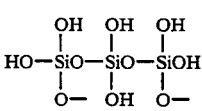  [Formula 10]

A polysiloxane film was also formed by the process abovementioned without washing with Freon 113 solvent.

The obtained siloxane monomolecular film 14, or polysiloxane film was firmly bonded to the surface of the back mirror 11 via chemical —SiO— bonds and did not separate at all. The obtained siloxane monomolecular film 14 or polysiloxane film had numerous —SiOH bonds on the surface. About seven times the number of hydroxyl groups were generated compared to the initial number of hydroxyl groups.

Figure 8:
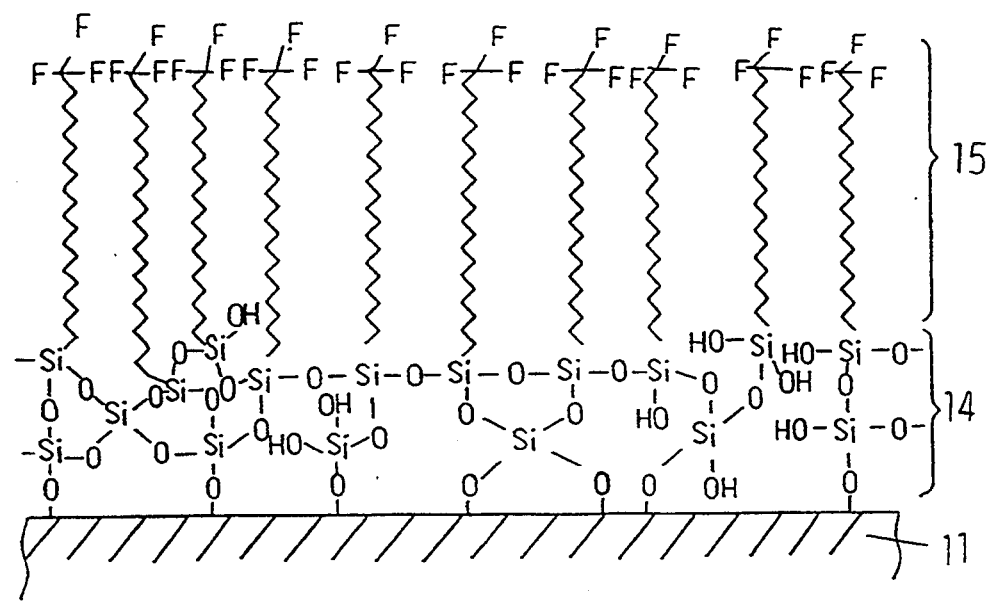
FIG. 8 is a sectional view showing a laminated layer film of a fluorocarbon based monomolecular film which is formed on the substrate of an inner layer film, which is enlarged to the molecular level.

The back mirror 11, on which surface the siloxane monomolecular film 14, or polysiloxane film, was formed, was left for one hour in a fluorocarbon adsorbing atmosphere in which the solution contained a non-aqueous solvent(Freon 113) in which 20% of $CF_3(CF_2)_7(CH_2)_2SiCl_3$ was vaporized. Then chemical bonds as shown in formula 5 were formed on the siloxane monomolecular film 14, or polysiloxane film, and a chemically adsorbed monomolecular film 15 containing fluorine as shown in FIG. 8 having a thickness of chemical adsorption about 1.5 nm was formed on the entire surface of the mirror by chemical bonding with inner layer of siloxane monomolecular film 14 or polysiloxane film.

A fluorocarbon based polymer film was also obtained by the process abovementioned without washing with a non-aqueous solvent.

The obtained monomolecular film and the obtained polymer film did not separate by a peel-off test. The back mirror in the example of the invention was used in a trial use test. According to the trial test, a drop of water of 3 mm in diameter did not adhere to the surface of back mirror at all. A dressing oil was applied to the surface of the back mirror to simulate contact with hair. The dressing oil was repelled, showing an oil-repellent effect, and the surface of the back mirror was not clouded at all.

EXAMPLE 3

Example 3 was carried out as in example 2 except for using polycarbonate resin instead of acrylic resin, i.e., tridecafluorooctyltrichlorosilane $CF_3(CF_2)_5(CH_2)_2$—$SiCl_3$ instead of heptadecafluorodecyltrichlorisilane.

EXAMPLE 4

Example 4 was carried out as in example 2 except for using polypropylene instead of the acrylic resin, i.e., perfluorododecyltrichlorosilane instead of heptadecafluorodecyltrichlorosilane.

EXAMPLE 5

Example 5 was carried out as in example 2 except for using ABS resin instead of acrylic resin.

EXAMPLE 6

Example 6 was carried out as in example 2 except for using epoxide resin instead of acrylic resin.

EXAMPLE 7

Example 7 was carried out as in example 2 except for using polyurethane resin instead of acrylic resin.

EXAMPLE 8

Example 8 was carried out as in example 2 except for using styrene-butadiene rubber resin instead of acrylic resin.

EXAMPLE 9

Example 9 was carried out by as in example 2 except for using butyl rubber resin instead of acrylic resin.

EXAMPLE 10

Example 10 was carried out as in example 2 except for using nitrite rubber resin instead of acrylic resin.

EXAMPLE 11

After a chemically adsorbed monomolecular film was formed by using 18-nonadecenyltrichlorosilane instead of heptadecafluorodecyltrichlorisilane as in example 2, an electron beam of 0.02 Mrads$^{-1}$, 300 keV was irradiated in a nitrogen atmosphere.

EXAMPLE 12

Example 12 was carried out as in example 1 except for using tetrachlorosilane instead of heptachlorosiloxane.

EXAMPLE 13

Example 13 was carried out as in example 2 except for using an oxidation treatment in which a substrate is dipped and held in concentrated sulfuric acid containing 10 wt % potassium dichromate.

COMPARATIVE EXAMPLE 1

A methanol solution containing 2 wt % of a silane coupling agent (heptadecafluorodecyltrimethoxysilane) was spin-coated on the surface of a polycarbonate resin and was dried at 120° C. for one hour.

COMPARATIVE EXAMPLE 2

A chemically adsorbed monomolecular film of heptadecafluorodecyltrichlorosilane was formed by using the acrylic resin of example 2 without oxidation.

COMPARATIVE EXAMPLE 3

A suspension of polytetrafluoroethylene was spray-coated on the surface of the acrylic resin of example 2, and was heated at 120° C. for one hour.

The contact angle of reagents which were used in examples 1 to 13 and comparative examples 1 to 3 against pure water and oil (Nisshin Salad Oil) were measured. The contact angle was measured just after a chemically adsorbed film, or a coating film was formed and after the films whose surfaces were rubbed about 10,000 times by a piece of cloth which was moistened with water. The contact angle is defined by JIS-K3211. The results are shown in table 1.

TABLE 1

| | Contact angle to water (°) | | Contact angle to oil (°) | |
|---|---|---|---|---|
| | initial value | after rubbing | initial value | after rubbing |
| Example 1 | 121 | 119 | 96 | 95 |
| Example 2 | 114 | 113 | 92 | 91 |
| Example 3 | 111 | 110 | 94 | 93 |
| Example 4 | 112 | 112 | 93 | 91 |
| Example 5 | 112 | 110 | 93 | 92 |
| Example 6 | 111 | 110 | 92 | 90 |
| Example 7 | 111 | 107 | 90 | 88 |
| Example 8 | 110 | 110 | 94 | 91 |
| Example 9 | 112 | 111 | 92 | 90 |
| Example 10 | 112 | 109 | 90 | 89 |
| Example 11 | 107 | 106 | 91 | 83 |
| Example 12 | 106 | 102 | 87 | 81 |
| Example 13 | 112 | 109 | 92 | 89 |
| Comparative Ex. 1 | 106 | 94 | 85 | 77 |
| Comparative Ex. 2 | 92 | 44 | 63 | 11 |
| Comparative Ex. 3 | 105 | 65 | 85 | 40 |

According to the results of table 1, samples of the invention maintained a water repellent property and an oil repellent property or a hydrophilic property even if the surface was washed and rubbed with a piece of cloth, which was moistened with water. However, the substrate of comparative example 2 and 3 did not keep a water repellent property and an oil repellent property after being washed by the same step abovementioned. The reagent of comparative example 2 in which the surface of the high molecular weight composite was not oxidized could not form a chemically adsorbed film having a siloxane bond. The substrate on whose surface a chemically adsorbed film having a fluorocarbon group was formed had an excellent contamination-proof property. After testing by rubbing, the reagent of example 1 dipped and held in salad oil and was wiped off with tissues. The oil which adhered to the reagent of example 1 was wiped off entirely. However, in comparative example 1, even after the reagent of comparative example 1 was wiped off with tissues several times, an oil film was formed on the surface of reagent, and the reagent was sticky.

The invention can be applied to an optical material. The transmittance of visible rays through the polycarbonate resin of example 3 was 92%. Before a chemically adsorbed monomolecular film was formed on the substrate, the ratio of transmittance was essentially the same. However, a sample which was coated with polytetrafluoroethylene as in comparative example 3, exhibited decreased transmissivity i.e., less than 50%, and the degree of transparency was lowered to that of a frosted glass.

EXAMPLE 14

A stainless steel kitchen knife (an Fe kitchen knife and a Cu kitchen knife are available.) having only a few hydroxyl groups was left in a gas atmosphere for about thirty minutes in which a material having a plurality of chlorosilyl groups e.g.. SiCl$_4$ (SiHCl$_3$, SiH$_2$Cl$_2$, Cl—(-SiCl$_2$O)$_n$—SiCl$_3$ (n represents an integer) was vaporized. Among the materials abovementioned, molecules of SiCl$_4$ are small and very active to hydroxyl groups and have a great effect on making a surface of a kitchen knife hydrophilic uniformly. A polysiloxane based film containing silanol groups was formed by a dehydrochlorination reaction with hydrophilic OH groups on the surface of kitchen knife and then by reacting with moisture contained in the air.

The film abovementioned was entirely bonded to the kitchen knife via chemical —SiO— bonds and did not separate at all except for by a decomposition reaction. The obtained polysiloxane film had numerous —SiOH bonds on the surface of the film. About 100 times the number of hydroxyl groups were generated compared to the number of hydroxyl groups originally present.

The kitchen knife, on which surface a polysiloxane film was formed, was left in an atmosphere for about one hour in which some of the solution was vaporized. The solution abovementioned was prepared by dissolving an adsorbent such as a material containing a fluorocarbon group and chlorosilane group, for example, $CF_3(CF_2)_7(CH_2)_2SiCl_3$, at about 10% in a non-aqueous solvent mixture of 80% n-hexdecane, 12% carbon tetrachloride, 8% chloroform solution. Then the kitchen knife was washed with a non-aqueous solution such as chloroform to remove unreacted material and then reacted with water or left in air to react with the moisture in the air. A $CF_3(CF_2)_7(CH_2)_2Si(O—)_3$ bond i.e., monolayer was formed on the siloxane film abovementioned formed on the surface of the kitchen knife, Thus a monomolecular film containing fluorine was formed on the whole surface of the kitchen knife by chemically bonding to a lower layer of a polysiloxane film having a thickness of chemical adsorption about 2.0 nm. The laminated film abovementioned did not separate at all by a cross cut test.

EXAMPLE 15

An aluminum pan which has a hydrophilic property but only a few hydroxyl groups was left in a gas atmosphere for about thirty minutes in which a material having a plurality of chlorosilyl groups e.g., $SiCl_4$ was dissolved, at a concentration of 10%, in a nonaqueous solvent such as chloroform, and vaporized. A dehydrochlorination reaction was brought about between some of the hydrophilic OH groups on the surface of the aluminum pan and the molecules were fixed on the surface of the aluminum pan via —SiO-bonds e.g., $Si(Cl)_3O—$ or $—OSi(Cl)_2O—$.

The aluminum pan was washed well with a non-aqueous solvent, e.g., chloroform to remove unreacted molecules of $SiCl_4$, and then with water to stabilize the residue chlorosilane groups. A siloxane monomolecular film such as $Si(OH)_3O—$ or $—OSi(OH)_2O—$ was formed on the surface of the aluminum pan.

The obtained monomolecular film was perfectly bonded to the surface of the aluminum pan via chemical —SiO— bonds and did not separate at all. The obtained monomolecular film had numerous —SiOH bonds on the surface of the monomolecular film. About three times the number of hydroxyl groups compared to the initial numbers of hydroxyl groups was generated.

The chloroform solution containing 50% adsorbent, e.g., $CF_3(CF_2)_7(CH_2)_2SiCl_3$, which is a material containing a fluorocarbon group and a chlorosilane group, was prepared by using a non-aqueous solvent. The aluminum pan on which surface the monomolecular film had numerous SiOH groups was left in the adsorbing vessel for about one hour where the solution abovementioned was placed. Then the aluminum pan was reacted with water or with moisture in air to form a bond of $CF_3(CF_2)_7(CH_2)_2Si(O—)_3$ on the surface of the aluminum pan, and a fluorocarbon based polymer film containing fluorine having a thickness of chemical adsorption about 2.0 nm was formed by chemical bonding with an inner layer of a siloxane monomolecular film on the whole surface of aluminum pan. The obtained polymer film did not separate at all by a peel-off test.

EXAMPLE 16

An iron frying pan which has a hydrophilic property, but a few hydroxyl groups, was left in an adsorbing vessel at room temperature for about thirty minutes where a solution dissolved 15% of $SiCl_4$ as a material containing a plurality of chlorosilyl groups in a chloroform solvent was introduced. A dehydrochlorination reaction was brought about between some hydrophilic —OH groups on the surface of the iron frying pan to form —SiO— groups. Then the frying pan was washed with water to react molecules of —SiCl or $SiCl_4$ which were unreacted at the surface of the frying pan to form a polysiloxane film on the surface of the frying pan.

The obtained polysiloxane film was perfectly bonded to the surface of the frying pan via chemical —SiO— bonds and did not separate at all. The obtained polysiloxane film had numerous —SiOH bonds on the surface of the film. About ten times the number of hydroxyl groups compared to the initial number of hydroxyl groups were generated.

The solution was prepared by using a non-aqueous solvent, and fluorocarbonsystem chlosilane adsorbent, for example, $CF_3(CF_2)_7(CH_2)_2SiCl_3$, containing a fluorocarbon group and a chlorosilane group. The frying pan, on which surface the monomolecular film had numerous —SiOH groups was formed, was left in the adsorbing room for one hour, where the solution abovementioned was vaporized, and then was reacted with water or with moisture in the air to form a $CF_3(CF_2)_7(CH_2)_2Si(O—)_3$ bond, and fluorocarbon based polymer film containing fluorine was formed by chemical bonding with a lower layer of a polysiloxane film on the whole surface of the frying pan having a thickness of about 10 nm. The obtained polymer film was not separated by peel-off test.

EXAMPLE 17

The chloroform solution, containing an adsorbent at a concentration of 5%, was prepared by using a non-aqueous solvent, e.g., $CF_3(CF_2)_7(CH_2)_2SiCl_3$, in which a fluorocarbon group and a chlorosilane group were contained. A ceramic coffee cup having a hydrophilic property was left in a gas atmosphere for one hour at room temperature where the solution abovementioned was vaporized and then was washed with a non-aqueous solution such as chloroform to remove unreacted material and then reacted with water or with moisture in the air. A $CF_3(CF_2)_7(CH_2)_2Si(O—)_3$ i.e., a fluorocarbon based monomolecular film having a thickness of 1.5 nm was formed on the entirely surface of the coffee cup. The obtained monomolecular film was transparent and was not separated at all by a peel-off test.

EXAMPLE 18

A ceramic plate which has a hydrophilic property was left in an adsorbent gas atmosphere for one hour at room temperature. The adsorbent solution was made of a non-aqueous solvent and a material having a fluorocarbon group and a chlorosilane group such as $CF_3(CF_2)_5(CH_2)_2SiCl_3$, and the adsorbent gas atmosphere was made by vaporizing the solution. Then the ceramic plate was reacted with water or with moisture in the air to form a $CF_3(CF_2)_5(CH_2)_2Si(O—)_3$ bond on the surface of the ceramic plate. Then a fluorocarbon based polymer film was formed on the whole surface having a thickness of about 10 nm. The obtained polymer film was not separated at all by a peel-off test.

According to the invention abovementioned, a chemically adsorbed laminated film can be formed effectively on various kinds of substrates such as plastic, ceramic and glass in a gas phase atmosphere. Further, a pinhole-free chemically adsorbed film having close adherence to the substrate can be formed uniformly in a short time effectively without using a dipping tank.

According to the invention, an inner siloxane based monomolecular film, or a polysiloxane film i.e., an inner siloxane polymer layer film, was formed in a gas phase atmosphere and then a chemically adsorbed monomolecular film or a polymer film having straight chain by hydrocarbon, was formed on the inner siloxane based monomolecular film, or polysiloxane film. Thus, the chemically adsorbed monomolecular film or polymer film can be laminated on various kinds of substrates, such as metal, plastic, ceramic and glass which have few active hydrogen groups such as hydroxyl groups, amino groups and imino groups on the surface of the substrate.

According to the invention, a dense, pinhole-free, extremely thin fluorocarbon based monomolecular film having an excellent water repellent property and oil repellent property, contamination-proof property, durability and uniform thickness can be formed on metallic substrates such as Al, Cu or stainless steel via a chemical bond by using a compound containing a fluorocarbon group and a chlorosilyl group as an adsorbent. Thus, a highly efficient fluorocarbon based ultra thin film having an excellent durability can be provided by the invention.

Therefore, a chemically adsorbed monomolecular film according to the invention can be applied to electronic products such as a hot plate and an electric rice cooker, automobiles, industrial equipment, glass, a lens for glasses which need to have a heat-plate resistant property, weather ability, and a friction-free ultra thin film coating.

Another enbodiment of the invention is to form a monomolecular film on the surface of a substrate by a gas phase method in a decreased pressure atmosphere. Some oxides, metals, ceramics, glass, plastic and semiconductors can be used as a material for the substrate. Of course, a plastic film on which surface abovementioned materials are deposited, or a laser disk, on which surface a recording material is applied, can be used as a substrate. A chemically adsorbed film can be formed densely on the substrate covered with hydrophilic groups.

A hydrocarbon group having an active hydrogen group such as a hydroxyl group, a carbonyl group, an imino group or an imino group can be used as a hydrophilic group. For example, a hydroxyl group can be prepared as a hydrophilic group by dipping and holding a substrate in a nitricacid solution and followed by washing with pure water. After the substrate is dried, it is placed in a vacuum vessel. When the desirable degree of a vacuum is obtained, a chemical adsorbent is introduced contacted with the surface of the substrate in a gas atmosphere to cause a chemical adsorption reaction. A chemical adsorbent having a high vapor pressure at room temperature can be used for the gasphase adsorbent by using an inert gas such as dehydrated and dried argon or nitrogen as a carrier gas. A chemical adsorbent in the liquid phase at room temperature can be used as vapor by heating higher than the boiling point or by bubbling dehydrated and dried argon and nitrogen as a carrier gas to pass through the chemical adsorbent. A chemical adsorbent in the solid state at room temperature can be provided by placing it in a crucible and heating higher than the boiling point to be vaporized. The chemical adsorbent having reactive silane groups, which reacted with the hydrophilic active hydrogen on the surface of the substrate, was carried to the surface of the substrate and formed a siloxane bond. Thus, a chemically adsorbed monomolecular film can be formed via the siloxane bond abovementioned. A reaction was carried out in a gas phase atmosphere i.e., in a decreased pressure atmosphere or non-aqueous and inert gas atmosphere, and hydrogen chloride which was generated by the chemical adsoption reaction were carried away from the surface of substrate rapidly by diffusing. As a result, the secondary chemical reaction such as slowing of the adsorbing reaction or corrosion of the substrate by hydrogen chloride can be prevented. The phenomena abovementioned is one of the advantages of the chemical adsorption in the gas phase. In the gas phase, the density of the thermal motion of the molecules which prevents a reactive product from diffusing is much lower than that in a liquid phase, and a reactive product can be diffused very rapidly. On a gas phase chemical adsorption, a hydrophilic group having an active hydrogen as a reaction site was used up by the adsorption reaction, the adsorbing reaction was terminated automatically and then a chemically adsorbed film was formed. After that, the vacuum vessel was evacuated to separate and remove molecules of unreacted chemical adsorbent which were adsorbed physically on the surface of the substrate. In the process abovementioned, heating the substrate at a temperature which does not decompose the chemically adsorbed monomolecular film is an effective means to promote separating and removing the molecules of the unreacted chemical adsorbent.

A silane based surface adsorbent having a chlorosilyl group ($-SiCl_nX_{3-n}$) or an alkoxysilane group ($-Si(OA)_nX_{3-n}$) at one end and a fluorocarbon group at another end can be used as a chemical adsorbent (where n represents an integer from one to three, X represents hydrogen, a lower alkyl group or a lower alkoxyl group, and A represents a lower alkyl group). Among the silane based surface adsorbents abovementioned, it is preferable to use a chlorosilane based surface adsorbent since a chemical reaction can be carried out at room temperature to form a chemically adsorbed monomolecular film. Among the chlorosilane based surface adsorbents, it is preferable to use a trichlorine-silicon chemical bond (where n represents 3) as adsorption molecules are formed via siloxane bonds. It is preferable to use a silane based surface adsorbent having a straight chain shape to improve the density of the adsorbing molecules. More particularly, it is preferable to use a chlorosilane based adsorbent represented as $CH_3-(R-)_m-SiCl_nX_{3-n}$, or $CF_3-(CF_2)_p-(R)_m-SiCl_nX_{3-n}$ (where p represents 0 or an integer, m represents 0 or 1, R represents a hydrocarbon group containing a methylene group, vinylene group ($-CH=CH-$), ethynylene group ($-C\equiv C-$), a silicon group ($Si-$), or an oxygen atom, ($-O-$), X represents hydrogen, a lower alkyl group or lower alkoxyl group, and n represents an integer from 1 to 3). More particularly, $CH_3(CH_2)_9SiCl_3$, $CH_3(CH_2)_{15}SiCl_3$, $CH_3CH_2O(CH_2)_{15}SiCl_3$, $CH_3(CH_2)_2Si(CH_3)_2(CH_2)_{15}SiCl_3$, $CF_3CH_2O(CH_2)_{15}SiCl_3$, $CF_3(CH_2)_2Si(CH_3)_2(CH_2)_{15}SiCl_3$, $F(CF_2)_4(CH_2)_2(Si(CH_3)_2(CH_2)_9SiCl_3$, $CF_3COO(CH_2)_{15}SiCl_3$, $CF_3(CF_2)_5(CH_2)_2SiCl_3$ can be used. Further, it is preferable that the R group in the above formula contains a vinylene group or an ethynylene group, since non-saturated bond can be polymerized by a catalyst, light or irradiation with a high energy beam to form a firmer monomolecular film having bonds between molecules. Further it is preferable to use a silane based surface agent containing fluorocarbon, since the silane surface agent containing fluorocarbon has an excellent water-repellent effect and electric insulation property.

Another embodiment of the invention concerns forming a laminated film by a gas phase method at a decreased pressure atmosphere. A material containing a straight carbon chain having a plurality of chemical bonds of chlorine and silicon (i.e., a $-SiCl_nX_{3-n}$ (chlorosilyl) group where n represents 1, 2, 3 and X represents a functional group) as a chemical adsorbent was bubbled using an inert gas such as dehydrated and dried argon or nitrogen as a carrier gas to carry to the surface of the substrate in the gas phase to be chemically adsorbed by exposing to the surface of substrate (adsorbing step). After the adsorbing step, a material containing unreacted chlorosilyl groups which were physically adsorbed to the surface of the substrate was separated or removed (removing step) by evacuating the vessel. Then the chlorine and silicon chemical bonds which were chemically adsorbed in a material was reacted with steam introduced to the surface of the substrate or reacted by introducing hydrogen gas and oxygen gas to the surface of the substrate and irradiating with ultraviolet rays to form a silanol group to form a monomolecular layer film. A process of forming a monomolecular adsorbed film comprised the steps abovementioned.

After the process of forming a monomolecular adsorbed film on which surface numerous hydroxyl groups exist, the chemically adsorbed monomolecular film can be laminated by repeating the step of forming a monomolecular adsorbed film (i.e., a step of forming a chemically adsorbed film). Thus, a monomolecular laminated film can be formed.

After forming a chemically adsorbed monomolecular film with an adsorbent having plurality of chlorosilane groups by the step abovementioned, a fluorocarbon monomolecular film can be formed by exposing the adsorbent to the surface of the chemically adsorbed film abovementioned in the gas phase by heating the silane based adsorbent containing a fluorocarbon or by bubbling the adsorbent with an inert gas such as dehydrated and dried argon or nitrogen as a carrier gas to chemically react with silanol groups contained on the surface of the chemically adsorbed film, and then a monomolecular laminated film can be formed. It is preferable to use the step abovementioned, since a silane based surface adsorbent containing a fluorocarbon can be densely and chemically adsorbed to the substrate on which surface has a few exposed hydroxyl groups. $SiCl_4$, $SiHCl_3$, $SiH_2Cl_2$, $(SiCl_2O)_nSiCl_3$, $H_k(R^1)_{3-k}Si(R^2)_nSiCl_m(R^3)_{3-m}$ can be used as a material having a plurality of chlorosilane groups. In general, a material having numerous Cl—Si bonds is preferable. A silane based adsorbent can be chemically adsorbed to the material abovementioned more densely. In the above formula, n represents an integer, k or m represents an integer from 1 to 3, $R^1$ or $R^3$ represents a lower alkyl group, $R^2$ represents a methylene group having a carbon number greater than 1. More particularly, it is preferable to use $SiCl_4$ as a material containing a chemical bond of chlorine and silicon since $SiCl_4$ are small and reactive to hydroxyl groups and have an excellent effect making the surface of a substrate hydrophilic uniformly.

A monomolecular film being one layer or a laminated monomolecular is called as a chemically adsorbed monomolecular film in this invention. In a laminated monomolecular film, a laminated layer is required to be chemically bonded to another laminated layer.

This invention will be explained more concretely by using in a condenser as a typical example.

EXAMPLE 19

A polypropylene film having a thickness of 4μm was washed and was put in a vacuum vessel. A vacuum pressure of $10^{-6}$ Torr was applied. Then an aluminum electrode was formed, having a thickness of about 100 nm, by vacuum sublimation deposition as a substrate 21. Then a surface of the substrate 21 was treated to form a hydroxyl group (—OH) as hydrophilic group. More concretely, a hydroxyl group was formed on the surface of the aluminum substrate 21 by introducing a small amount of a hydrogen gas and oxygen gas as a reactive gas on the surface of the substrate 21 and irradiating using ultraviolet rays from a mercury lamp. A steam gas can be used as the reactive gas. The supply of reactive gas was stopped and a vacuum of $10^{-6}$ Torr was applied. Then chemical adsorption was carried out using $CF_3(CF_2)_7(CH_2)_2SiCl_3$ as the silane based surface adsorbent having a straight carbon chain. Since the chlorosilane based surface adsorbent is liquid at room temperature, it is preferable to introduce the chlorosilane based surface adsorbent in a vacuum vessel by heating or by bubbling the chlorosilane based adsorbent with an inert gas such as dehydrated and dry argon or nitrogen as a carrier gas to carry to the surface of the substrate by fine supply pipe. A dehydrochlorination reaction was brought about between hydroxyl groups (—OH) on the surface of the substrate and the chlorine atom of the silyl group (SiCl) of the chlorosilane based surface adsorbent to form a bond as represented in formula 11 on the whole surface of the substrate.

[Formula 11]

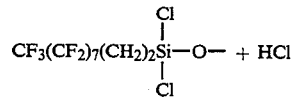

It requires about ten to thirty minutes for adsorbing. Then a supply of adsorbent was stopped to evacuate again to separate and remove unreacted molecules of a chemical adsorbent which was adsorbed physically on the surface of substrate 21. During the step of separating and removing unreacted molecules of chemical adsorbent abovementioned, heating the substrate 21 at about 120° C., which does not decompose the chemically adsorbed monomolecular film, is very effective to promote separating and removing unreacted molecules of chemical adsorbent and saves treating time.

Then, steam was supplied to the surface of the substrate 21 to react with unreacted chemical bond of chlorine and silicon to form silanol groups (—SiOH). Moisture from the air can be used instead of steam or a lot of steam can be supplied positively. Pure water can be used. The reaction formula of hydrolysis is shown in formula 12.

[Formula 12]

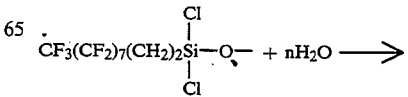

-continued

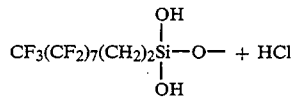  + HCl

A monomolecular film 22 can be formed by forming a siloxane bond by drying and dehydrating.

Figure 9:
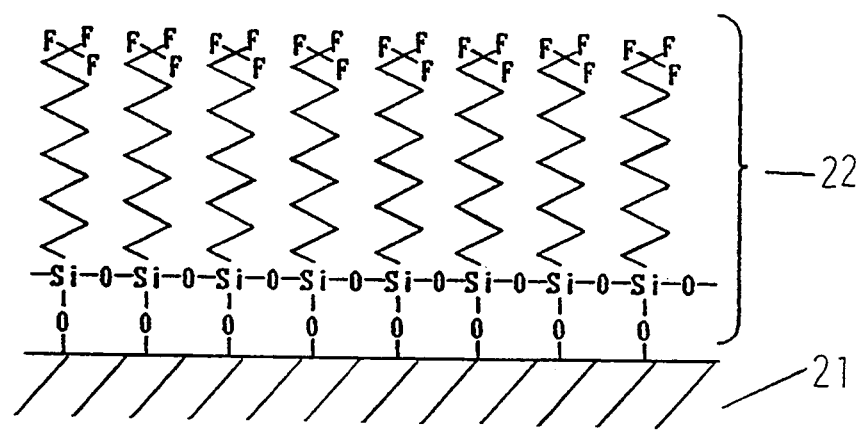
FIG. 9 is a sectional view showing the forming of a monomolecular film of the invention, which is enlarged to a molecular level.
Figure 10:
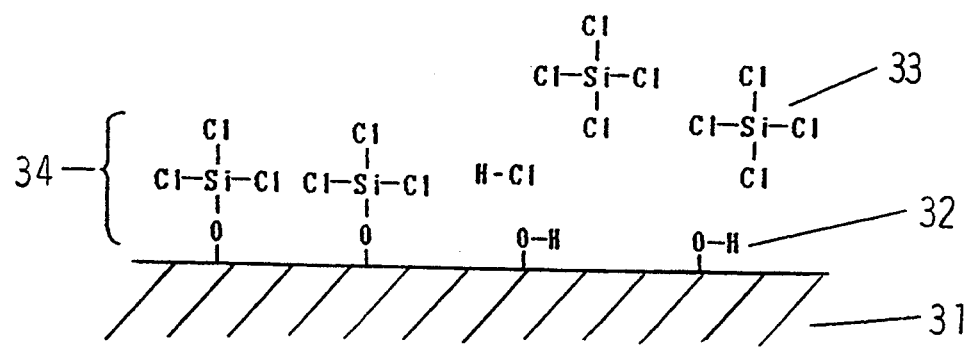
FIG. 10 is a sectional view showing the forming of an inner layer film on the surface of substrate, which is enlarged to a molecular level.

One layer of monomolecular film 22 containing fluorine can be formed on an aluminum substrate 21 as shown in FIG. 9. The thickness of the chemically adsorbed film 22 was 1.5 nm judging from the molecular structure.

If the above step is omitted and the substrate was taken out in the aim coating moisture, the formula of the dehydrating decomposition is as shown in formula 13 and a chemically adsorbed polymer film can be formed.

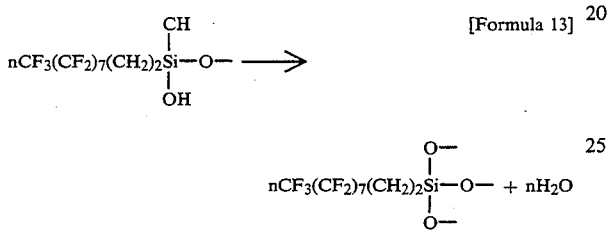

[Formula 13]

The monomolecular film 22 or polymer film was firmly and chemically bonded to the substrate and did not separate at all. Further, the aluminum deposition film formed on the substrate 21 was not damaged at all.

A condenser was formed on the monomolecular film 22 by depositing 10 nm of an aluminum film by vacuum evaporation deposition as the opposite electrode and electric property of the condenser was measured. According to the result, the condenser has a lower leak current and higher electric insulation property compared to that which was made of the monomolecular film formed by the liquid phase. The obtained condenser had a satisfactory result, and the characteristic variation by a moving ion did not occur.

EXAMPLE 20

A polishing glass as a substrate 31, which was washed and put in vacuum vessel to reach to a vacuum of $10^{-6}$ Torr, and an aluminum electrode of about 100 nm in thickness was formed by vacuum deposition. Then the surface of the substrate was treated to form a hydroxyl group as hydrophilic group on the surface.

More concretely, a hydroxyl group 32 was formed on the surface of the aluminum substrate 31 by spraying oxygen gas and hydrogen gas as the reactive gas little by little to the surface of the substrate 31 and irradiating with ultraviolet rays with a mercury lamp and the evacuating the vacuum vessel. A steam gas can be used as the reactive gas as in example 1.

The supplying of reactive gas was stopped to evacuate to a vacuum of $10^{-6}$ Torr. Then $SiCl_4$ containing a trichlorosilyl group as a material having a plurality of chlorosilyl groups ($-SiCl_nX_{3-n}$ group where n represents 1, 2, 3, X represents a functional group) was put in the vacuum vessel by bubbling an inert gas such as dehydrated and dried argon or nitrogen as a carrier gas in the $SiCl_4$, and the obtained gas was carried out by a thin pipe to the surface of the substrate for about ten minutes to carry out the adsorbing reaction.

A chlorosilyl system monomolecular film 34 of a material containing a trichlorosilyl group was formed by a dehydrochlorination reaction between a hydroxyl group 32 having a hydrophilic property formed on the surface of the substrate 31 as shown in FIG. 2 and the chlorine atom of the trichlorosilyl group. By using $SiCl_4$ as a material containing plurality of chlorosilyl groups, a dehydrochlorination reaction was brought about on the surface of the substrate 31 which has a few hydrophilic OH groups 32 for fixing molecules on the surface of the substrate via —SiO— bonds as shown in formula 14 and 15.

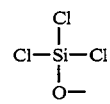

[Formula 14]

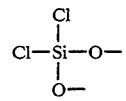

[Formula 15]

Where, in general, unreacted $SiCl_4$ is physically adsorbed to a chlorosilyl monomolecular film. Then evacuation is carried again to separate and remove the unreacted $SiCl_4$ abovementioned.

Figure 11:
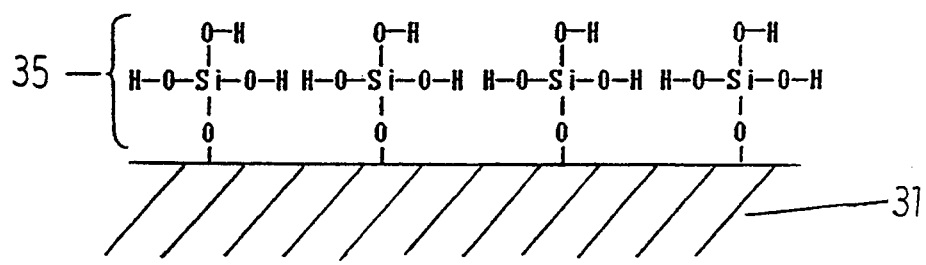
FIG. 11 is a sectional view showing the forming of an inner layer film on the surface of a substrate, which is enlarged to a molecular level.

A silanol group was formed by reacting the unreacted chlorosilyl group of the chemically adsorbed chlorosilyl monomolecular film with steam, which was introduced to the surface of the substrate, or by reacting with hydrogen gas and oxygen gas, which were introduced to the surface of the substrate and irradiating with ultraviolet rays. Then a siloxane monomolecular layer film 35 can be formed on the surface of the substrate (formula 16 to 17) as shown in FIG. 11.

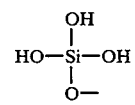

[Formula 16]

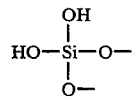

[Formula 17]

The obtained monomolecular film 35 was perfectly bonded to the surface of the substrate 31 via covalent bonds and did not separate at all. The obtained siloxane monomolecular film 35 had numerous —Si—OH bonds on the surface. About three times the number of hydroxyl groups were generated on surface of film compared to the initial number of hydroxyl groups.

Figure 12:
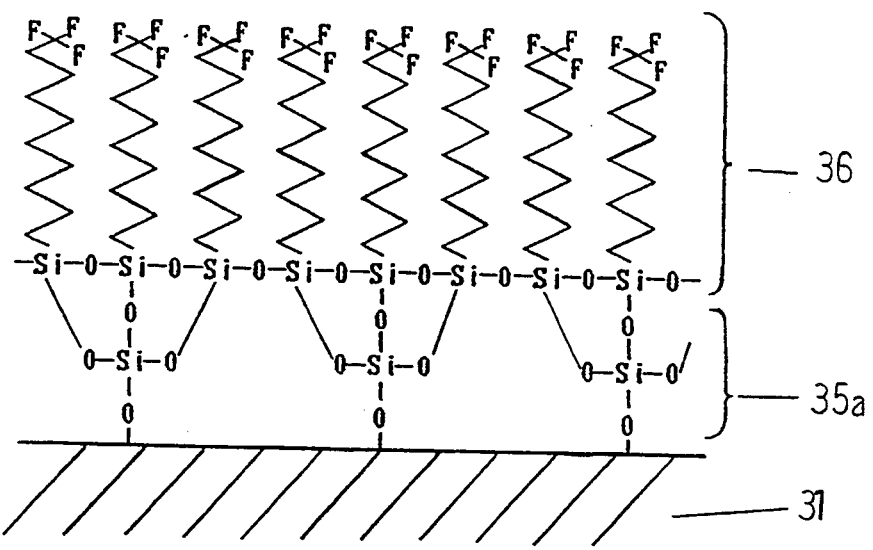
FIG. 12 is a sectional view showing a laminated layer on a substrate, which is enlarged to molecular level.

Chemical adsorption was carried out by using a chlorosilane based surface adsorbent having straight carbon chain such as $CF_3(CF_2)_7(C_2)_2SiCl_3$ which was mentioned in example 19. Bubbling was carried out by passing an inert gas such as dehydrated and dried argon or nitrogen as a carrier gas through the chlorosilane based surface adsorbent in a vacuum vessel. The obtained gas was brought to the surface of the substrate 11 by a fine pipe, on which surface the fluorocarbon system monomolecular film 36 was chemically adsorbed for ten to thirty minutes. The bond represented in formula 18 was formed on the surface of the siloxane monomolecular film 35a on the whole surface of the substrate 11, to form a chemically adsorbed monomolecular film 36 containing fluorine and having a thickness of about 2.0 nm, which was chemically bonded to a lower layer of the siloxane monomolecular film 35a as shown in FIG. 12.

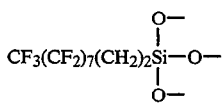
[Formula 18]

The reaction process was carried out as shown in formulas 1 to 3. Further, the obtained monomolecular film was not separated by a peel-off test. By carrying out the process as in example 19, an opposite electrode was used to form a condenser. The characteristics of the condenser were evaluated and almost the same characteristics of example 19 or more excellent characteristic was obtained. According to the obtained results, the density of the chemically adsorbed monomolecular film was high.

In example 19, one layer of monomolecular film was formed. In example 20, a laminated layer of a silane based surface adsorbent containing a fluorine on one layer of a siloxane monomolecular film was shown. However, the effect of the chemically adsorbed monomolecular film of the invention was not changed by laminating several layers of the chemically adsorbed monomolecular film. According to the invention, a monomolecular film having a desirable uniform thickness can be obtained by selectively chosing the length of the chain portion of adsorbed monomolecular film or by laminating the monomolecular film, and that is a very excellent utility.

In the example abovementioned, $CF_3(CF_2)_7(CH_2)SiCl_3$ was used as the chlorosilane based surface adsorbent containing fluorine. Further, the hardness of the monomolecular film can be improved by adding or incorporating a vinylene group (—CH=CH—) or an ethynylene group as a carbon-carbon triple bond to the R portion of the chlorosilane based surface adsorbent, represented as $CF_3—(CF_2)_n—(R)_m—SiX_pCl_{3-p}$ (wherein n represents 0 or an integer, R represents an alkyl group, a vinyl group, an ethynyl group or a substituted group containing a silicon atom or an oxygen atom, m represents 0 or 1, X represents H, an alkyl group, an alkoxyl group, an alkyl substituted group containing fluorine or an alkoxyl substituted group containing fluorine, and p represents 0, 1, 2 or 3), to cross-link by irradiating with an electron beam of 5 mega rad (Mrad) after the monomolecular film is formed.

Trichlorosilane based surface adsorbents such as $CF_3CH_2O(CH_2)_{15}SiCl_3$, $CF_3(CH_2)_2Si(CH_3)_2(CH_2)_{15}SiCl_3$, $F(CF_2)_4(CH_2)_2Si(CH_3)_2(CH_2)_9SiCl_3$, $CF_3COO(CH_2)_{15}SiCl_3$, $CF_3(CF_2)_5(CH_2)_2SiCl_3$ and chlorosilane based surface adsorbents such as $CF_3CH_2O(CH_2)_{15}Si(CH_3)_2Cl$, $CF_3(CH_2)_2Si(CH_3)_2(CH_2)_{15}Si(CH_3)_2Cl$, $CF_3CH_2O(CH_2)_{15}Si(CH_3)Cl_2$, $CF_3COO(CH_2)_{15}Si(CH_3)_2Cl$ can be used as a fluorocarbon based surface adsorbent. By using alkoxysilane based surface adsorbents such as $CF_3(CF_2)_7(CH_2)_2Si(OCH_3)_3$, $CF_3CH_2O(CH_2)_{15}Si(OCH_3)_3$, the similar effect was obtained by heating the surface adsorbent solution.

A chemically adsorbed monomolecular film can be obtained in a gas phase atmosphere by using chlorosilane based adsorbents containing a fluorocarbon group such as $CH_3(CH_2)_9SiCl_3$, $CH_3(CH_2)_{15}SiCl_3$, $CH_3CH_2O(CH_2)_{15}SiCl_3$, $CH_3(CH_2)_2Si(CH_3)_2(CH_2)_{15}SiCl_3$. According to the embodiments of forming a monomolecular film as in example 19, and example 20, a chemically adsorbed film will have little contamination since chemical adsorption is carried out in a gas phase atmosphere. Thus, the obtained monomolecular film is suitable for uses which requires surface control such as in an electronic device. Further, in layering other kinds of thin films, since chemical adsorption is carried out in a gas phase atmosphere, it is possible to form a thin film successively in the same vessel and the number of man-days and the amount of costs are effectively decreased. The method of forming a monomolecular film abovementioned has an excellent practical value for making a tunnel device or a condenser which requires a film having a uniform thickness.

According to the method for forming a monomolecular laminated film of the invention, a chlorine atom is substituted with a hydroxyl group using a molecule containing straight carbon chain having a highly reactive chlorosilyl group. Thus, a more dense chemically adsorbed monomolecular film can be formed than by forming a single layer of the monomolecular layer film.

As has been shown, the invention is greatly beneficial to industry.

The invention may be embodied in other specific forms without departing from the spirit or essential characteristics thereof. The present embodiment is to be considered in all respects as illustrative and not restrictive, the scope of the invention being indicated by the appended claims rather than by the foregoing description and all changes which come within the meaning and range of equivalency of the claims are intended to be embraced therein.

We claim;

1. A method of forming a chemically adsorbed film in a gas phase on a surface of a substrate containing active hydrogen groups comprising contacting a silane based surface adsorbent having a reactive silyl group at one end of a straight chain molecule with the surface of said substrate and initiating a condensation reaction in a gas phase atmosphere, wherein said gas phase is generated by heating said silane based surface adsorbent, or bubbling said silane based surface adsorbent or a solution containing said silane bases surface adsorbent by using a dry inert gas as a carrier.

2. The method of forming the chemically adsorbed film according to claim 1, wherein a chlorosilane based adsorbent or an alkoxyl silane based adsorbent is used as the silane based surface adsorbent and a dehydrochlorination reaction or a de-alcohol reaction is carried out as condensation reaction.

3. The method of forming the chemically adsorbed film according to claim 2, wherein after the dehydrochlorination reaction, unadsorbed chlorosilane based adsorbent on the surface of the substrate is washed and removed with a non-aqueous solution to form a monomolecular adsorbed film and the adsorbed unreacted silane based adsorbent is reacted with water.

4. The method of forming the chemically adsorbed film according to claim 2, wherein after the dehydrochlorination reaction, the surface adsorbent a straight chain molecule as the chlorosilane based adsorbent is reacted with water to form a chemically adsorbed polymer film.

5. The method of forming the chemically adsorbed film according to claims 2, 3 or 4, wherein the chlorosilane based surface adsorbent contains a straight fluorocarbon chain molecule or a portion of straight hydrocarbon chain molecule substituted by a —$CF_2$— group or a fluorocarbon based group.

6. The method of forming the chemically adsorbed film according to claims 2, 3 or 4, wherein the chlorosilane based adsorbent is $CF_3$—$(CF_2)_n$—$(R)_m$—$SiX_pCl_{3-p}$ and wherein n represents 0 or an integer, R represents an alkylene group, a vinylene group, an ethynylene group or a substituted group containing a silicon atom or an oxygen atom, m represents 0 or 1, X represents H, an alkyl group, an alkoxyl group, an alkyl substituted group containing fluorine or an alkoxyl substituted group containing fluorine, and p represents 0, 1, 2 or 3.

7. The method of forming the chemically adsorbed film according to one of claims 1 to 4, wherein the substrate is selected from the group consisting of metal, ceramics, glass, plastic, a semiconductor, an inorganic shaped solid and an organic shaped solid.

8. The method of forming the chemically adsorbed film according to one of claims 1 to 4, wherein the substrate is plastic and the substrate surface is hydrolyzed by treating with plasma containing oxygen or within a corona atmosphere.

9. The method of forming the chemically adsorbed film according to claim 1, wherein the surface of the substrate is contacted with an alkoxyl silane based surface adsorbent and the substrate is heated to at least about 50° C. to initiate the condensation reaction.

10. A method of forming a chemically adsorbed film comprising initiating a dehydrochlorination reaction between a substrate surface containing active hydrogen groups and an adsorbent gas of a material containing a plurality of chlorosilyl groups, washing and removing unreacted adsorbent with a non-aqueous solvent, forming a siloxane based monomolecular inner layer film containing a plurality of silanol groups on the surface of the substrate by reacting the inner layer with water, initiating a dehydrochlorination reaction between the inner layer film and an adsorbent gas of a material containing a straight chain group and a chlorosilane group at one end to form an outer layer film, washing and removing the unreacted adsorbent from the outer layer film with a non-aqueous solvent to form a laminated monomolecular outer layer film, and reacting the outer layer with water.

11. A method of forming a chemically adsorbed film comprising initiating a dehydrochlorination reaction between a surface of a substrate containing active hydrogen groups and an adsorbent gas to form an inner layer film by using an adsorbent gas of a material containing a plurality of chlorosilyl groups, forming a siloxane based polymer inner layer film containing a plurality of silanol groups on a surface of the substrate by reacting with water, initiating a dehydrochlorination reaction between an active hydrogen atom of the surface of the inner layer film and an adsorbent gas of a material containing a straight chain group and a chlorosilane group at one end to form an outer layer film, washing and removing unreacted adsorbent from the outer layer film with a non-aqueous solvent, and reacting the outer layer with water.

12. A method of forming a chemically adsorbed film comprising contacting an adsorbent gas of a material containing a plurality of chlorosilyl groups with a surface of a substrate containing active hydrogen groups to initiate a dehydrochlorination reaction between said active hydrogen groups and said adsorbent gas to form an inner monomolecular layer film, washing unadsorbed adsorbent with a non-aqueous solvent, reacting the inner layer with water to form a siloxane based monomolecular inner layer film containing a plurality of silanol groups on the surface of the substrate, contacting an adsorbent gas of a material containing a straight chain group and a chlorosilane group at one end with the surface of the inner layer film to form an outer layer, reacting the outer layer with water to form a laminated polymer outer layer film.

13. A method of forming a chemically adsorbed film comprising contacting an adsorbent gas of a material containing a plurality of chlorosilyl groups with a surface of a substrate containing active hydrogen groups and bringing about a dehydrochlorination reaction between said active hydrogen groups and said adsorbent gas to form an inner layer film, reacting said inner layer with water to form a polysiloxane inner layer film containing a plurality of silanol groups, contacting an adsorbent gas of a material containing straight chain molecules having chlorosilane groups at one end with said inner layer film to form a laminated polymer outer layer film, and reacting to stabilize the outer layer with water.

14. The method of forming the chemically adsorbed film according to claims 10, 11, 12 or 13, wherein the adsorbent gas of a material containing a plurality of chlorosilyl groups comprises at least one compound selected from the group consisting of $SiCl_4$, $SiHCl_3$, $SiH_2Cl_2$ or Cl—$(SiCl_2O)_n$—$SiCl_3$ wherein n represents an integer.

15. The method of forming the chemically adsorbed film according to one of claims 1 to 4, wherein the chemically adsorbed film is formed on the surface of the substrate having active hydrogen groups by placing said substrate in a vacuum vessel at decreased pressure or in a vacuum vessel having a dry atmosphere and contacting in a gas phase a silane based surface adsorbent having a reactive silyl group at one end with said surface of said substrate to bring about a dehydrochloration reaction.

16. The method of forming the chemically adsorbed film according to claim 15, wherein the vacuum vessel is at a decreased pressure lower than at least $10^{-5}$ Torr.

17. The method of forming the chemically adsorbed film according to claim 15, wherein a reactive gas contacts the substrate to react the unreacted —Si—Cl groups of the chemically adsorbed silane based surface adsorbent after an exhaust step.

18. The method of forming the chemically adsorbed film according to claim 15, wherein moisture in the air is used as the reactive gas to hydrolyze the unreacted —Si—Cl groups of the chemically adsorbed silane based surface adsorbent.

19. The method of forming the chemically adsorbed film according to claim 15, wherein the silane based surface adsorbent is $CF_3$—$(CF_2)_p$—$(R)_m$—$SiCl_nX_{3-n}$, wherein p represents 0 or an integer, m represents 0 or 1, R represents a hydrocarbon group containing a methylene group, vinylene group (—CH=CH—), an ethynylene group (—C≡C—), a silicon group (—Si), or an oxygen atom (—O—), X represents a hydrogen atom, a lower alkyl group or a lower alkoxyl group, n represents 0, 1 or 2.

* * * * *